United States Patent [19]

Swetly

[11] 4,046,879

[45] Sept. 6, 1977

[54] ANTIVIRAL COMPOSITIONS

[75] Inventor: Peter Swetly, Vienna, Austria

[73] Assignee: Boehringer Ingelheim GmbH, Ingelheim am Rhein, Germany

[21] Appl. No.: 662,374

[22] Filed: Mar. 1, 1976

[30] Foreign Application Priority Data

Mar. 5, 1975 Germany .............................. 2509531

[51] Int. Cl.$^2$ ............................................. A61K 31/70
[52] U.S. Cl. .................................... 424/180; 424/128
[58] Field of Search ......................................... 424/180

[56] References Cited

U.S. PATENT DOCUMENTS

| 3,819,830 | 6/1974 | Yoshimura et al. | 424/180 |
| 3,849,553 | 11/1974 | Dea et al. | 424/180 |
| 3,948,886 | 4/1976 | Shuman et al. | 424/180 |

*Primary Examiner*—Sam Rosen
*Attorney, Agent, or Firm*—Hammond & Littell

[57] ABSTRACT

A topical pharmaceutical antiviral composition consisting essentially of an inert pharmaceutical carrier or diluent, a complex-former for bivalent cations, and a 5'-triphosphate of a nucleoside or deoxyribonucleoside.

4 Claims, No Drawings

ANTIVIRAL COMPOSITIONS

This invention relates to novel topical antiviral compositions containing a complex-former for bivalent cations and a 5'-triphosphate of a nucleoside or deoxyribonucleoside, as well as to a method of treating topical virus infections therewith.

More particularly, the present invention relates to novel antiviral compositions which are especially effective against the viruses of the family of picornaviridae, such as rhinoviruses, enteroviruses and caliciviruses, consisting of one or more complexing agents for bivalent cations and one or more nucleoside or deoxynucleoside triphosphates, optionally in combination with another active ingredient, for instance, an agent which constricts swollen mucous membranes, such as 2-(5,6,7,8-tetrahydro-1-naphthylamino)-1-imidazoline hydrochloride, or with detergents, preferably in the form of a neutral solution.

The novel, stable antiviral compositions of the present invention are prepared by simply uniformly distributing one or more of the complex-formers for bivalent cations and one or more of the nucleoside or deoxynucleoside triphosphates, and optionally also another active ingredient, in a suitable inert carrier; for instance, by dissolving the ingredients in water, ethanol or ethanol/water, or by uniformly admixing them with a powder such as talcum, or by blending them into an ointment base.

Examples of suitable nucleoside or deoxyribonucleoside triphosphates are substituted pyrimidine or purine bases bonded to ribose or deoxyribose, such as the 5'-triphosphates of cytidine, cytosine-deoxyriboside, thymidine, uridine, adenosine, adenine deoxyriboside, guanosine, guanidine deoxyriboside or inosine.

Examples of suitable complex-formers for bivalent cations are: Condensed phosphates and soluble salts thereof, especially the alkali metal salts, such as the sodium or potassium salts of pyrophosphoric acid, tetrametaphosphoric acid, trimetaphosphoric acid, tripolyphosphoric acid, nucleoside diphosphates, deoxyribonucleoside diphosphates; Amino acids and the soluble salts thereof, especially the alkali metal salts, such as the sodium or potassium salts of β-alanine-N,N-diacetic acid, aminobarbituric acid-N,N-diacetic acid, 2-amino-benzoic acid-N,N-diacetic acid, β-aminoethyl-phosphonic acid-N,N-diacetic acid, β-aminoethyl-sulfonic acid-N,N-diacetic acid, aminomethyl-phosphonic acid-N,N-diacetic acid, amino-diacetic acid, aminodipropionic acid, nitrilo-triacetic acid, 2-sulfoaniline-diacetic acid, 1,2-diaminocyclohexane-N,N-tetraacetic acid, 1,3-diaminocyclohexane-N,N-tetraacetic acid, 1,4-diaminocyclohexane-N,N-tetraacetic acid, ethylenediaminetetraacetic acid, N-benzylethylenediamine-triacetic acid, ethylenediaminetetrapropionic acid, methylamino-N,N-diacetic acid, trimethylenediaminetetraacetic acid, tetramethylenediamine-tetraacetic acid, pentamethylenediamine-tetraacetic acid, ethyleneglycol-bis-(β-aminoethylether)-N,N'-tetraacetic acid, asparagine, asparaginic acid, glycine, histidine, proline, tryptophane, valine, SH-glutathione or γ-carboxyglutamic acid; Heterocyclic compounds containing nitrogen, such as 1,10-O-phenanthroline and derivatives thereof; dicarboxylic acids and soluble salts thereof, especially the alkali metal salts, such as the sodium or potassium salts of oxalic acid or citric acid; Hydroxycarboxylic acids and soluble salts thereof, especially the alkali metal salts, such as the sodium or potassium salts of malic acid; Diketones, such as acetylacetone, benzoylacetone, benzoyltrifluoroacetone, dibenzoylmethane, 2-furoyl-benzoylmethane or 2-thienoyl-2-furoylmethane; Phenolic compounds, such as 8-oxyquinoline; Dyes, such as Eriochrome Black T, Eriochrome Black A or Eriochrome Black R; Sugar-amino acid-compounds, such as fructose-glycine or fructoseasparaginic acid; and Vitamins or vitamin derivatives, such as pyridoxyl-glycine, pyridoxyl-amine, pyridoxyl-valine, pyridoxyl-threonine, pyridoxyl-tyrosine, pyridoxyl-tryptophane, pyridoxyl-isonicotinic acid-hydrazide or ascorbic acid and sodium potassium-salts of ascorbic acid.

The compositions of this invention may contain 0.5 to 100 mgm of complex-former component and 0.05 to 20 mgm of nucleoside triphosphate or deoxynucleoside triphosphate per gram of total weight of composition.

However, the use of adenosine triphosphate with the complexing agent sodium pyrophosphate is of special advantage. The concentration of adenosine triphosphate in the composition advantageously ranges from 0.05 to 20 mgm/gm of the antiviral composition, and the concentration of sodium pyrophosphate advantageously from 0.5 to 100 mgm/gm of the antiviral composition in an aqueous and/or alcoholic medium.

An especially advantageous antiviral composition for topical pharmaceutical application is, however, obtained, when it is combined with an agent which constricts swollen mucous membranes, such as 2-(5,6,7,8-tetrahydro-1-naphthylamino)-2-imidazoline hydrochloride.

For this purpose the concentration of adenosine triphosphate, for example, ranges from 0.05 to 5 mgm/ml, preferably from 0.1 to 1 mgm/ml. The pH-value can vary between 6.0 and 8.5, preferably, however, between 6.5 and 8.

The concentration of the complexing agent depends on the particular stability constant for complexes with bivalent cations. Here, the ion class is different for various virus classes; the most important are $Mg^{++}$, $Ca^{++}$, $Zn^{++}$. For medication against rhinoviruses, the causative agent of the common cold, the complexing agents showing a high affinity to $Mg^{++}$ are especially active in combination with adenosine triphosphate. The concentration for pyrophosphate amounts to from 0.5 to 50 mgm/ml, preferably, however, from 10 to 25 mgm/ml. Thus, the particular object of the present invention is an antiviral composition which is especially active against rhinovirus, foot and mouth disease virus, echovirus, coxsackie A and B viruses and calici-virus.

The biological activity of the novel antiviral composition was tested as follows:

1. Based on the stability of the radioactive-labeled ribonucleic acid complement of rhinoviruses, the decrease of intact viruses in a reaction mixture was investigated. The reaction was carried out by incubation for 30 minutes at 36° C at pH = 7.4 of $P^{32}$-labeled rhinovirus with the antiviral composition, followed by determination of:

a. The trichloroacetic acid-precipitable radioactive material;

b. The radioactive material sedimenting in a sucrose gradient at 160 S (Svedberg) = sedimentation constant of the intact virus;

c. The radioactive RNA (ribonucleic acid) sedimenting at 30 S = sedimentation constant of the viral RNA; and d. The radioactive material banding at a density of 1.40 to 1.42 gm/cm³ in a cesium chloride equilibrium density gradient (position of the rhinovirus type 2).

The following results were obtained:

Sodium adenosine triphosphate in a concentration of 0.25 millimol in the presence of 2 millimols of sodium pyrophosphate causes a decomposition of more than 90% of the rhinovirus nucleic acid to trichloroacetic acid-soluble, low molecular weight oligonucleotides. The sedimentation constant of these oligonucleotides is below 3 S (Svedberg) in comparison with the sedimentation constant of the infectious rhinovirus ribonucleic acid, which is about 30 S. Neither at 160 S, the sedimentation constant of the intact virus, nor at 1.40 to 1.42 gm/cm³ in cesium chloride, radioactive-labeled material could be found.

2. Purified, unlabeled virus was incubated with a mixture of complexing agents and nucleoside triphosphate, as described under 1 above, and the infectiousness of corresponding dilutions of the treated viruses was compared with untreated viruses in a plaque-test on cultures of human tissue cells. Here, a decrease in infectious virus to 0.01 percent of the original value could be observed after treatment with adenosine triphosphate and pyrophosphate.

3. The essential role of the hydrolyzable $\beta$-$\gamma$-oxygen-bridge in the nucleoside triphosphate for the autocatalytic degradation of the rhinovirus-ribonucleic acid was shown by:

a. Removal of the $P^{32}$-labeled phosphate radical in the $\gamma$-position from adenosine triphosphate during the reaction with rhinovirus in a $Mg^{++}$-ion free medium with formation of adenosine diphosphate and rhinovirus-bonded $P^{32}$.

b. Inactivity of adenosine diphosphate to induce the autocatalytic RNA-degradation.

c. Adenosine-imido-diphosphate, an analog of adenosine triphosphate, the $\beta$-$\gamma$-oxygen-bridge of which is replaced by an —NH—group and which cannot be hydrolyzed in this position, is completely ineffective in initiating the autocatalytic inactivation of the rhinoviruses.

4. Furthermore, the enzymatic character of the rhinovirus ribonucleic acid decomposition is supported by the strong temperature dependence of the reaction (at 0° or 20° C no reaction, above 30° C complete decomposition).

5. In all cases an equimolar (with regard to complexing agent and nucleoside triphosphate) addition of $Mg^{++}$-ions to the reaction mixture prevents the decomposition.

6. The synergistic effect of the complexing agent (e.g. sodium pyrophosphate) and phosphorylating agent (e.g. adenosine triphosphate) was shown by means of the inducible decomposition of radioactive-labeled rhinovirus ribonucleic acid: Aliquotes (10⁶ plaque-forming units) of purified rhinoviruses, the ribonucleic acid of which had been labeled with phosphorus-32, were incubated for 30 minutes with 5 n moles of adenosine triphosphate, either separately or with increasing quantities of sodium pyrophosphate at a pH-value of 7.6 and 36° C. As control values sodium pyrophosphate was used in various concentrations without adenosine triphosphate. The result is summarized in the following table:

| Adenosine triphosphate concentration (n moles)* | Sodium pyrophosphate concentration (n moles)* | % degradation of the viral ribonucleic acid |
|---|---|---|
| 5 | 0 | <7.5 |
| 5 | 50 | 10 |
| 5 | 250 | 67 |
| 5 | 500 | 94 |
| 0 | 0 | <7.5 |
| 0 | 50 | <10 |
| 0 | 250 | <10 |
| 0 | 500 | <10 |

*n moles = $10^{-9}$ mol

These results show that the concentration of sodium pyrophosphate has to exceed a limiting value so that the inducing activity of the adenosine triphosphate on the decomposition of the virusribonucleic acid can take effect and thus a synergistic effect of both components is present.

The morphologic alterations of the virus structure could also be determined by electron microscope. Here, it was clearly shown that the protective virus capsid structure opened after treatment with pyrophosphate and adenosine triphosphate.

The following examples further illustrate the present invention and will enable others skilled in the art to understand it more completely. It should be understood, however, that the invention is not limited solely to the particular examples given below.

EXAMPLE 1

Solution with pyrophosphate and adenosine triphosphate

The solution was compounded from the following ingredients:

| | | |
|---|---|---|
| Adenosine triphosphate (sodium salt) | 5.0 | parts |
| Pyrophosphate (sodium salt) | 100.0 | " |
| 2-(5,6,7,8-Tetrahydro-1-naphthyl-amino)-2-imidazoline hydrochloride | 10.0 | " |
| Benzalkonium chloride | 10.0 | " |
| Sodium dihydrogen phosphate | 10.0 | " |
| Disodium hydrogen phosphate | 20.0 | " |
| Tylose | 10.0 | " |
| Distilled water q.s.ad | 10,000.0 | " |
| | | by vol. |

Preparation

The adenosine triphosphate, the pyrophosphate, the benzalkonium chloride and the tylose were dissolved in a sufficient amount of distilled water, the buffer substances were added, and the resulting solution was diluted with distilled water to the indicated volume.

EXAMPLE 2

Solution with adenosine triphosphate

The solution was compounded from the following ingredients:

| | | |
|---|---|---|
| Adenosine triphosphate (sodium salt) | 5.0 | parts |
| Adenosine diphosphate (sodium salt) | 25.0 | " |
| Sodium dihydrogen phosphate | 10.0 | " |
| Disodium hydrogen phosphate | 20.0 | " |
| Benzalkonium chloride | 10.0 | " |
| Tylose | 10.0 | " |
| Distilled water q.s.ad | 10,000.0 | " |
| | | by vol. |

Preparation

The adenosine triphosphate and the adenosine diphosphate were freeze-dried from a neutral aqueous solution and dissolved in the aqueous solution of the remaining components as a lyophilized powder a short time before use.

EXAMPLE 3

Solution of guanosine triphosphate

The solution was compounded from the following ingredients:

| | | | |
|---|---|---|---|
| Guanosine triphosphate (sodium salt) | | 0.5 | parts |
| Pyrophosphate (sodium salt) | | 100.0 | " |
| Benzalkonium chloride | | 5.0 | " |
| Sodium hydroxide solution ad pH = 7.4 | qu.s. | | |
| Distilled water | q.s.ad | 10,000.0 | " |
| | | | by vol. |

Preparation

The guanosine triphosphate, the pyrophosphate and the benzalkonium chloride were dissolved in a sufficient amount of distilled water, adjusted to a pH of 7.4 with an aqueous sodium hydroxide solution and diluted with distilled water to the indicated volume.

EXAMPLE 4

Gel with adenosine triphosphate and ethylenediaminetetraacetic acid

The gel composition was compounded from the following ingredients:

| | | | |
|---|---|---|---|
| Adenosine triphosphate (sodium salt) | | 0.025 | parts |
| Ethylenediaminetetraacetic acid (sodium salt) | | 0.050 | " |
| Benzalkonium chloride | | 0.100 | " |
| Carboxypolymethylene | | 0.700 | " |
| Triethylamine | | 0.800 | " |
| Glycerin | | 5.0 | " |
| Cremophor RH 40 (emulsifier) | | 5.0 | " |
| Distilled water | q.s.ad | 100.0 | " |
| | | | by vol. |

Preparation

An aqueous solution of the adenosine triphosphate, the ethylenediaminetetraacetic acid, the benzalkonium chloride, the triethanolamine and the glycerin was stirred into an aqueous solution of the carboxypolymethylene.

EXAMPLE 5

Cream with adenosine triphosphate and pyrophosphate

The cream was compounded from the following ingredients:

| | | | |
|---|---|---|---|
| Adenosine triphosphate (sodium salt) | | 0.5 | parts |
| Pyrophosphate (sodium salt) | | 0.5 | " |
| Isopropyl myristate | | 7.0 | " |
| Tween 60 (surfactant) | | 2.0 | " |
| Span 60 (surfactant) | | 2.0 | " |
| Lanette 0 (cream base) | | 7.0 | " |
| Benzalkonium chloride | | 0.1 | " |
| Distilled water | q.s.ad. | 100.0 | " |
| | | | by vol. |

Preparation

The benzalkonium chloride and the pyrophosphate were dissolved in the distilled water which had been heated to 70° C (solution I). The adenosine triphosphate was suspended in the molten mixture of the isopropylmyristate, the Tween 60, Span 60 and the Lanette O (suspension II). Suspension II was emulsified into solution I.

EXAMPLE 6

Ointment with uridine triphosphate and sodium citrate

The ointment was compounded from the following ingredients:

| | | | |
|---|---|---|---|
| Uridine triphosphate (sodium salt) | | 0.025 | parts |
| Sodium citrate | | 0.25 | " |
| Anhydrous wool grease | | 6.0 | " |
| Subliquid paraffin | | 30.0 | " |
| Vaseline | q.s.ad | 100.0 | " |

Preparation

The sodium citrate, the uridine triphosphate, the anhydrous wool grease, the paraffin and the vaseline were melted together, and the molten mixture was blended until uniform.

EXAMPLE 7

Foam aerosol with adenosine phosphate and pyridoxylamine

The aerosol composition was compounded from the following ingredients:

| | | |
|---|---|---|
| Adenosine triphosphate (sodium salt) | 0.1 | parts |
| Pyridoxylamine | 0.1 | " |
| Cremorphor (emulsifier) | 0.9 | " |
| Tween 80 (surfactant) | 1.3 | " |
| Texapon N 25 (wetting agent) | 1.0 | " |
| Ethanol 96% | 20.0 | " |
| Distilled water | 61.8 | " |
| Propellant (frigen 12/114 = 60:40) | 15.0 | " |

Preparation

The adenosine triphosphate and the pyridoxylamine were dissolved in the distilled water (solution I). The Cremophor, the Tween and the Texapon were dissolved in the aqueous ethanol (solution II). Solution I was stirred into solution II, and the obtained concentrate was filled into aerosol cans which were closed with a valve and pressurized with the propellant gas.

EXAMPLE 8

Aerosol with adenosine triphosphate and pyridoxylamine

The aerosol composition was compounded from the following ingredients:

| | | |
|---|---|---|
| Adenosine triphosphate (sodium salt) | 0.2 | parts |
| Pyridoxyl amine | 0.25 | " |
| Cremophor (emulsifier) | 0.9 | " |
| Tween 80 (surfactant) | 1.3 | " |
| Ethanol 96% | 20.0 | " |
| Distilled water | 61.8 | " |
| Propellant gas mixture | 15.0 | " |

Preparation

Analogous to Example 7.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A topical antiviral pharmaceutical composition consisting essentially of an inert carrier and uniformly distributed therein 0.05 to 20 mgm of at least one nucleoside triphosphate or deoxynucleoside triphosphate and 0.5 to 100 mgm of at least one complex-former for bivalent cations per gram of total weight of said composition.

2. An antiviral composition of claim 1, wherein said complex-former is sodium pyrophosphate, adenosine diphosphate, sodium citrate, ethylenediaminetetraacetic acid or pyridoxylamine, and said triphosphate is adenosine triphosphate, guanosine triphosphate, cytidine phosphate or the triphosphate of a corresponding deoxyribonucleoside.

3. An antiviral composition of claim 1, wherein said complex-former is sodium pyrophosphate and said triphosphate is adenosine triphosphate.

4. The method of combatting topical virus infections, which comprises treating the infection with a composition of claim 1.

* * * * *